United States Patent [19]

Drypen et al.

[11] Patent Number: 5,318,544

[45] Date of Patent: Jun. 7, 1994

[54] METERING SYRINGE

[75] Inventors: John Drypen, Redford Township; Charles E. Steele, Canton, both of Mich.

[73] Assignee: Kerr Manufacturing Company, Romulus, Mich.

[21] Appl. No.: 964,045

[22] Filed: Oct. 20, 1992

[51] Int. Cl.$^5$ .................................... A61M 5/00
[52] U.S. Cl. .................................... 604/210; 604/211
[58] Field of Search ................. 604/187, 207–211, 604/218, 224, 227

[56] References Cited

U.S. PATENT DOCUMENTS

| | | | |
|---|---|---|---|
| 1,393,720 | 10/1921 | Lomas | 604/210 |
| 2,373,520 | 4/1945 | Wallin | 604/210 |
| 2,409,656 | 10/1946 | Austin | 604/210 |
| 2,502,639 | 4/1950 | Blake | 604/210 |
| 2,695,023 | 11/1954 | Brown | 604/210 |
| 2,707,954 | 5/1954 | Kas | 604/210 |
| 4,466,426 | 8/1984 | Blackman | 604/210 X |
| 4,475,905 | 10/1984 | Himmelstrup | 604/208 |
| 4,654,035 | 3/1987 | Ando | 604/210 |
| 4,710,179 | 12/1987 | Haber et al. | 604/211 |
| 4,810,249 | 3/1989 | Haber et al. | 604/210 |
| 4,929,238 | 5/1990 | Baum | 604/208 |
| 5,024,661 | 6/1991 | Wender et al. | 604/110 |

FOREIGN PATENT DOCUMENTS 2561925   10/1985   France ................. 604/208

*Primary Examiner*—C. Fred Rosenbaum
*Assistant Examiner*—Frank Wilkens
*Attorney, Agent, or Firm*—Wood, Herron & Evans

[57] ABSTRACT

A syringe for metering fluid in which a plunger contains a plurality of stop surfaces which contact a stop on a syringe tube. The stop surfaces are linearly displaced from each other along a longitudinal axis of the plunger by distances corresponding to predetermined volumes of fluid to be metered. The stop surfaces are also angularly displaced about the longitudinal axis of the plunger so that incremental rotation of the plunger permits successive stop surfaces to limit plunger motion, thereby effecting a precise metering of the fluid.

5 Claims, 2 Drawing Sheets

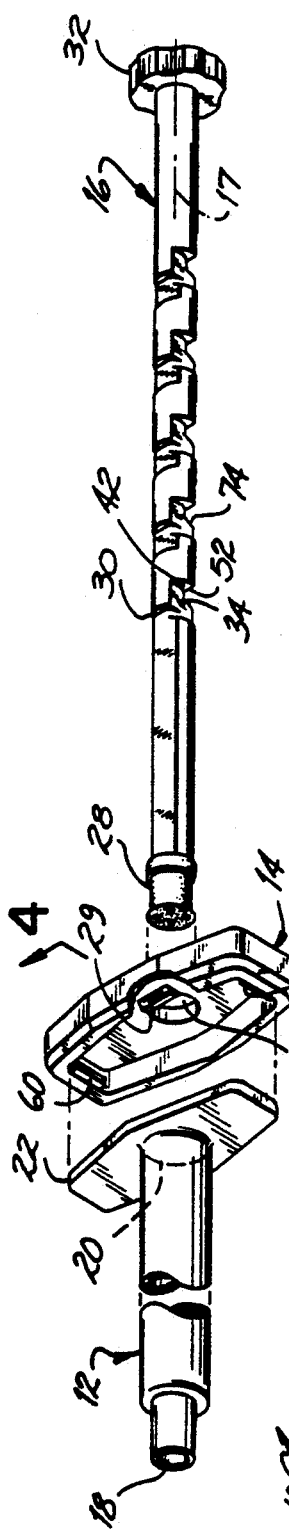
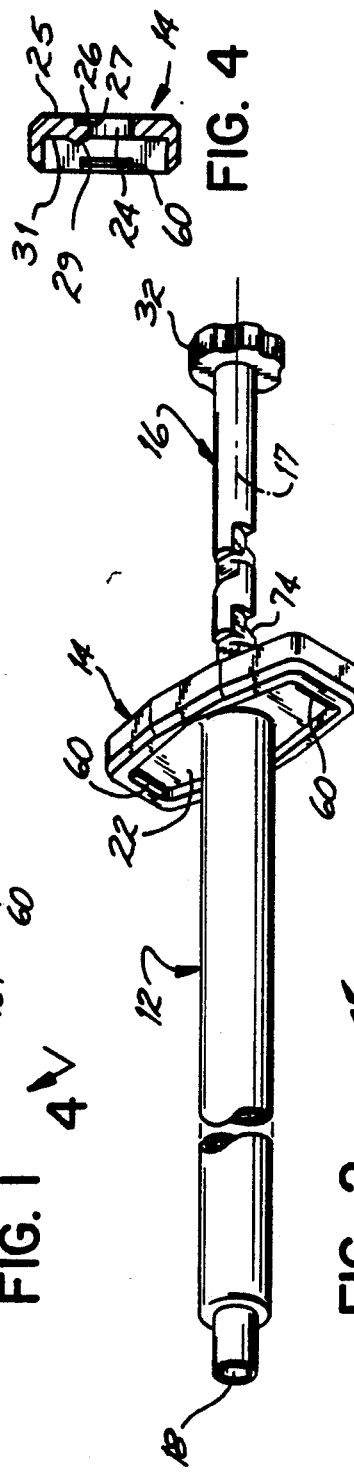
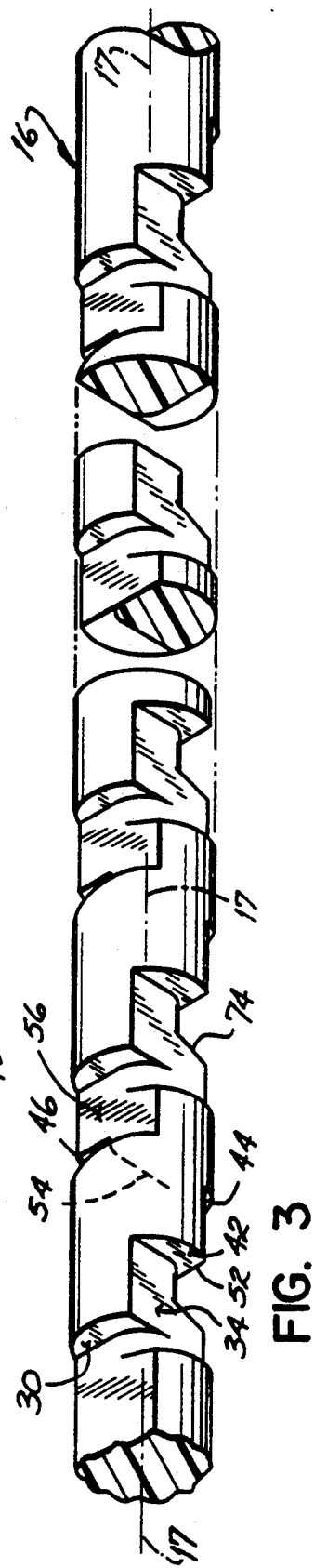

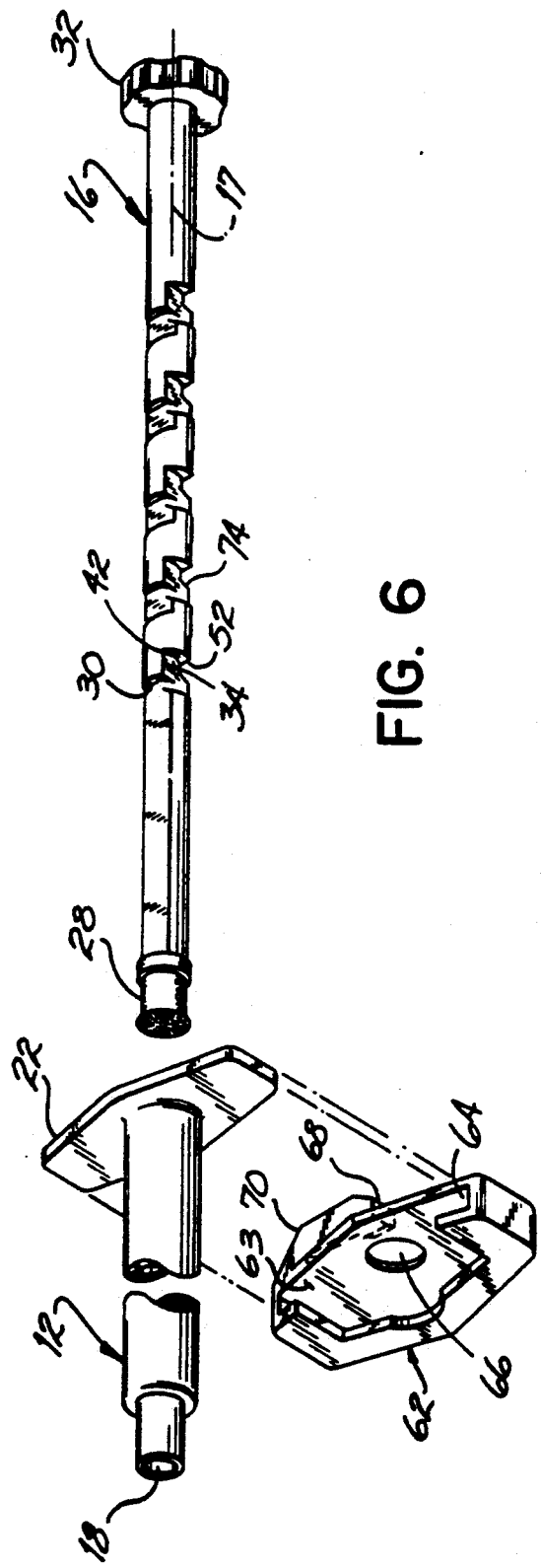
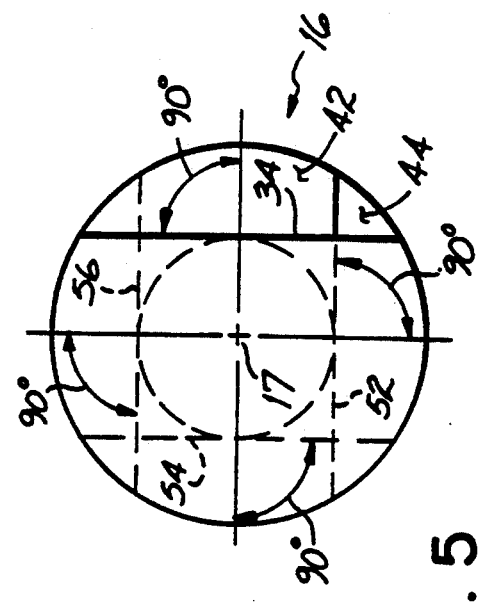
FIG. 6
FIG. 5

METERING SYRINGE

BACKGROUND OF THE INVENTION

1. Field of the Invention

The invention relates to a syringe and more particularly to a syringe for easily metering predetermined volumes of fluid therefrom.

2. Description of the Related Art

In many situations, it is necessary to either fill a syringe with a precise volume of fluid or discharge a precise volume of fluid from the syringe. Other situations require that precise volumes of fluid be incrementally discharged over a period of time.

In order to control the volumetric intake to and discharge from a syringe, a syringe tube typically has a visual scale calibrated in volumetric units. Therefore, a plunger inside the syringe tube is translated along the scale a distance corresponding to the desired fluid volume.

While such a scale is functional, circumstances may arise which make the scale difficult to read. For example, the fluid may have a color which does not contrast with the color of the scale. Further, there may be distortions in the scale from manufacturing. Variations in the eyesight of the person using the syringe may also make the scale difficult to read and use. Photosensitive fluids require an opaque syringe tube which makes it impossible to use a syringe tube scale. Finally, the discharge of successive precise volumes of fluid requires precise control of the plunger relative to the scale so that too much or too little fluid is not metered through the syringe. Precise control becomes more difficult with smaller dosages which require smaller plunger movements.

SUMMARY OF THE INVENTION

To overcome the disadvantages of existing syringes, a primary object of the present invention is to provide a syringe for metering precise volumes of fluid without having to use a visual volumetric scale. According to the principles of the present invention, a syringe has a syringe tube with an orifice at one end and an opening at the other end. A plunger is slidably located in the opening, and a clip functioning as a positive stop is attached to the syringe tube at the opening. The plunger contains a plurality of stop surfaces which are angularly displaced about a longitudinal axis 17 of the plunger. Further, the stop surfaces are linearly displaced along the longitudinal axis. Translation of the plunger brings a first stop surface into contact with the stop, the plunger is then rotated to release the first stop surface from the stop, thereby permitting the plunger to be translated until a second stop surface contacts the stop. During translation of the plunger, a predetermined volume of fluid is metered through the orifice.

One advantage of the claimed syringe is that predetermined volumes of fluid may be precisely metered through the orifice without having to read a scale of volumetric units and without requiring the user of the syringe to precisely control the stopping action of the plunger. In addition, volumetric quantities of a photosensitive fluid may be precisely metered from a syringe made of an opaque material.

These and other objects and advantages of the present invention will become more readily apparent during the following detailed description taken in conjunction with the drawings herein.

BRIEF DESCRIPTION OF THE DRAWINGS

FIG. 1 illustrates the component parts of a first embodiment of the syringe.

FIG. 2 illustrates an assembled syringe utilizing the component parts of the first embodiment.

FIG. 3 is an expanded view of the syringe plunger.

FIG. 4 is a cross-sectional view taken along the lines 4—4 of FIG. 1.

FIG. 5 is a diagrammatic view illustrating the angular relationship between the stop and relief surfaces.

FIG. 6 illustrates the component parts of a second embodiment of the syringe.

DETAILED DESCRIPTION

FIGS. 1-4 illustrate one embodiment of the invention. A syringe 10 is comprised of a syringe tube 12, a clip 14, and a metering plunger 16. The syringe tube 12 has an orifice 18 at one end and an opening 20 at an opposite end. Depending on the application, the orifice 18 may be in the one end of the syringe tube 12 or at one end of an injection needle which may be inserted in the one end of the syringe tube 12 The clip 14 is located proximate to the opening 20 and is attached to a flange 22 by means of clips 60 located on opposing sides of the clip 14. The clip 14 has an opening 24 concentric with the opening 20. The opening 24 is generally cylindrical but has a stop 26 which is a flat surface relieved from the outer surface 25. The stop 26 has an area bounded by an arc identical to the circumference of the opening 24 and an edge 27 defining a chord joining ends of the arc. The area of the stop 26 truncates the generally circular area of the opening 24. A reinforcing member 29 is located on an inner surface 31 of the clip 14 opposite the stop 26 thereby strengthening the clip 14 behind the stop 26.

The plunger 16 has a rubber tip 28 attached to one end which functions to prevent fluid from passing by the rubber tip and out of the opening 20. The cross-sectional shape of plunger 16 along its longitudinal axis is substantially the same as the shape of the opening 24. The plunger 16 is inserted through the opening 24 of the clip 14 and the opening 20 and is slidably located within the syringe tube 12. Translation of the plunger 16 within the syringe tube effects a transfer of fluid through the orifice 18.

By applying a longitudinal force to a knob 32 on the other end of the plunger 16, the plunger is translated through the syringe tube 12 until a first stop surface 30 contacts the stop 26. The longitudinal force is removed, and the plunger 16 is rotated using knob 32 until relief surface 34 contacts stop 26. Thereafter, by reapplying the longitudinal force to knob 32, the plunger 16 is moved forward in the syringe tube 12 to meter out a subsequent volume of fluid until stop surface 42 contacts the stop 26. As will be appreciated, if the application of the longitudinal force continues while the knob 32 is rotated, the stop surface 30 may lose contact with the stop 26 immediately before the relief surface 34 comes into full contact with the stop 26. At that point, the relief surface 34 is able to translate past the stop 26 until the second stop surface 42 contacts the stop 26. Relief surface 34 is a flat surface intersecting stop surfaces 30, 42 and extends in a direction generally parallel to the longitudinal axis 17 of the plunger 16. Relief surface 34 truncates the generally circular cross-sectional of the plunger 16, so that the cross-sectional shape of the plunger 16 is substantially the same as the shape of the opening 24. In either situation, the syringe is effective to me a precise volume of fluid during the plunger translation between stop surfaces. The second stop surface 42 is angularly displaced about and linearly displaced a predetermined distance along the longitudinal axis 17 from the first stop surface 30. Displacement of the plunger through that predetermined distance meters of a volume of fluid through the orifice 18. The metered volume of fluid is proportional to the linear displacement between the first and second stop surfaces. The plunger 16 has a plurality of stop surfaces angularly displaced about and linearly displaced along its longitudinal axis thereby permitting a user of the syringe to successively meter precise quantities of fluid from the syringe.

In the illustrated embodiment, rotation of the knob 32 through 90° will present a new relief surface to the stop 26 as well as a new stop surface. Therefore, as illustrated in FIG. 3, during one complete rotation of the plunger 16, that is, over four successive 90° rotations of the knob 32, four stop surfaces 30, 42, 44, and 46 and four relief surfaces 34, 52, 54, and 56 will be presented to the stop 26. As shown diagrammatically in FIG. 5, the relief surfaces 34, 52, 54, and 56 are angularly displaced from each other about the longitudinal axis 17 by 90° and the relief surfaces 34, 52, 54 and 56 are successively, equally spaced around the longitudinal axis 17 of the plunger 16. Similarly, stop surfaces 42 and 44 illustrated in FIG. 5 and the other stop surfaces which not illustrated are angularly displaced from each other about the longitudinal axis by 90°. The stop surfaces 42 and 44 illustrated in FIG. 5 and the other stop surfaces which are not illustrated are successively, equally spaced around the longitudinal axis 17 of the plunger 16.

As will be appreciated by those who are skilled in the art, it may be desired that the knob be turned 120°, 180° or some other rotational increment between translations of the plunger 16. In those situations, the angular displacements about the longitudinal axis 17 angularly separating the stop surfaces are changed until the desired number of stop surfaces and intersecting relief surfaces per one revolution is achieved. The linear displacements along the longitudinal axis 17 between the stop surfaces determines the volume of fluid to be metered with each plunger translation between stop surfaces. The stop surfaces may be equally spaced along the longitudinal axis thereby providing equal volumes of fluid with each plunger translation between stop surfaces. Alternatively, some therapies may require different dosages or fluid volumes over a period of time, and the spacing between stop surfaces along the longitudinal axis may be varied to accommodate the requirement of different dosages.

FIG. 5 illustrates an alternative embodiment in which a clip 62 has a peripheral groove 64 adapted to receive the flange 22 of a typical syringe tube 12. The clip 62 has a cylindrical hole 66 sized to receive the diameter of the plunger 16. The clip 62 further includes a stop 68 at the free end of a flexible arm 70 which at its other end is integral with the rear wall 63 of the clip. Flexible arm 70 biases the stop 68 to a location over the hole 66 and against the plunger 16 so that it resiliently contacts the stop surfaces on the plunger 16. The stop 68 is movable relative to the clip 62 in a direction perpendicular to the longitudinal axis 17 toward and away from the plunger 16. Therefore, when the plunger 16 is withdrawn from the syringe tube 12, the stop 68 contacts an inclined surface 74 on the plunger, which cams the stop away from the plunger deflecting arm 70, thereby permitting the plunger to be removed from the syringe tube with a single translation through the syringe tube. In contrast, to remove the plunger 16 from the syringe tube 12 using the clip 14 of FIG. 1, translation of the plunger out of the syringe tube will cause the inclined surface 74 to contact the reinforcing member 29 thereby providing a positive stop of the plunger translation. The plunger must then be rotated until a relief surface is aligned with the opening in the clip 62. Therefore the plunger is removed by a series of precise rotational and translational motions which are the opposite of the motions used to insert the plunger 16 into the syringe tube 12. The precise control of the plunger translation in a direction out of the syringe tube may be used to meter fluid into the syringe.

While the invention has been illustrated in some detail according to the preferred embodiments shown in the accompanying details, and while the preferred embodiments have been described in some detail, there is no intention to thus limit the invention to such detail. On the contrary, it is intended to cover all modifications, alterations, and equivalents falling within the spirit and scope of the appended claims.

What is claimed is:

1. A syringe for metering fluid, said syringe comprising:
    a syringe tube for holding the fluid and having an orifice at one end for discharging the fluid and a generally circular opening at an opposite end, said generally circular opening including a stop edge forming a chord across said generally circular opening; and
    a plunger slidably located in said openings of said syringe tube, said plunger having a longitudinal axis and a plurality of stop surfaces approximately perpendicular to said longitudinal axis and angularly displaced about said longitudinal axis from adjacent stop surfaces, said plunger further having a plurality of flat relief surfaces approximately parallel to said longitudinal axis and extending between and intersecting adjacent stop surfaces, said plunger having a cross-sectional shape along said longitudinal axis substantially the same as said generally circular opening with said stop edge forming said chord across said generally circular opening.

2. The syringe of claim 1 wherein said syringe tube further includes a clip releasably connected to a flange at said opposite end of said syringe tube, said clip having said generally circular opening for receiving said plunger.

3. The syringe of claim 2 wherein said stop edge is flexibly attached to said clip and, said stop edge is biased against said plunger so that said stop edge contacts said stop and relief surfaces.

4. A syringe for metering fluid comprising:
    a syringe tube for holding the fluid and having
    an orifice at one end for discharging the fluid, and
    a generally circular opening at an opposite end, said generally circular opening including a stop edge forming a chord across said generally circular opening, and
    a plunger slidably located in said opening of said syringe tube, said plunger having
    a longitudinal axis, a plurality of stop surfaces approximately perpendicular to said longitudinal axis, said plurality of stop surfaces being angularly disposed from each other and equally spaced around said longitudinal axis, and a plurality of flat relief surfaces approximately parallel to said longitudinal axis and extending between and intersecting adjacent stop surfaces, said plurality of flat relief surfaces being angularly displaced from each other and equally spaced around said longitudinal axis, said stop surfaces and said flat relief surfaces being spaced with respect to said longitudinal axis to form a cross-sectional shape of said plunger along said longitudinal axis substantially the same as said generally circular opening with said stop edge forming said chord across said generally circular opening.

5. A syringe for metering fluid comprising:

a syringe tube for holding the fluid and having an orifice at one end for discharging the fluid, and a generally circular opening at an opposite end, said generally circular opening including a stop edge forming a chord across said generally circular opening, and a plunger slidably located in said opening of said syringe tube, said plunger having a longitudinal axis, a plurality of stop surfaces approximately perpendicular to said longitudinal axis, said plurality of stop surfaces being angularly displaced from each other and successively, equally spaced around said longitudinal axis, and a plurality of flat relief surfaces approximately parallel to said longitudinal axis and extending between and intersecting adjacent stop surfaces, said plurality of flat surfaces being angularly displaced from each other and successively, equally spaced around said longitudinal axis, whereby one of said stop surfaces contacts said stop edge in response to a translation of said plunger thereby metering a predetermined volume of fluid from said syringe, and said one of said stop surfaces loses contact with said stop edge in response to a rotation of said plunger thereby permitting one of said relief surfaces to translate past said stop edge until an adjacent stop surface contacts said stop edge.

* * * * *